United States Patent [19]

Vanney et al.

[11] Patent Number: 5,571,175
[45] Date of Patent: Nov. 5, 1996

[54] SUTURE GUARD FOR PROSTHETIC HEART VALVE

[75] Inventors: Guy Vanney, Blaine; Kurt D. Krueger, Stacy; Michael J. Girard, Lino Lakes, all of Minn.

[73] Assignee: St. Jude Medical, Inc., St. Paul, Minn.

[21] Appl. No.: 487,497

[22] Filed: Jun. 7, 1995

[51] Int. Cl.⁶ ........................................ A61F 2/24
[52] U.S. Cl. ............................................. 623/2
[58] Field of Search .................. 623/2, 900; 606/148

[56] References Cited

U.S. PATENT DOCUMENTS

| | | |
|---|---|---|
| 3,546,710 | 12/1966 | Shumakov et al. . |
| 3,574,865 | 4/1971 | Hamaker . |
| 3,625,220 | 12/1971 | Engelsher ............................ 606/233 |
| 3,996,623 | 12/1976 | Kaster ................................... 623/2 |
| 4,233,690 | 11/1980 | Akins . |
| 4,665,906 | 5/1987 | Jervis . |

FOREIGN PATENT DOCUMENTS

| | | |
|---|---|---|
| 1180087 | 11/1964 | Germany . |
| 8900841 | 2/1989 | WIPO ................................ 623/2 |

*Primary Examiner*—David H. Willse
*Attorney, Agent, or Firm*—Hallie A. Finucane

[57] ABSTRACT

An artificial heart valve prosthesis for use in a heart includes an orifice defining a lumen therethrough for blood flow. An occluder is carried in the orifice and is movable between an open position which allows blood flow through the lumen and a closed position in which flow through the lumen is blocked. A suture cuff coupled to the orifice extends around an outer circumference of the orifice and is used for attaching the heart valve to a heart tissue annulus using sutures. The sutures are knotted proximate the suture cuff to secure the cuff to the annulus. A suture guard is coupled to the suture cuff and is movable between an open position in which the suture knot is exposed and a closed position in which the suture, suture knot and suture cuff are covered.

18 Claims, 19 Drawing Sheets

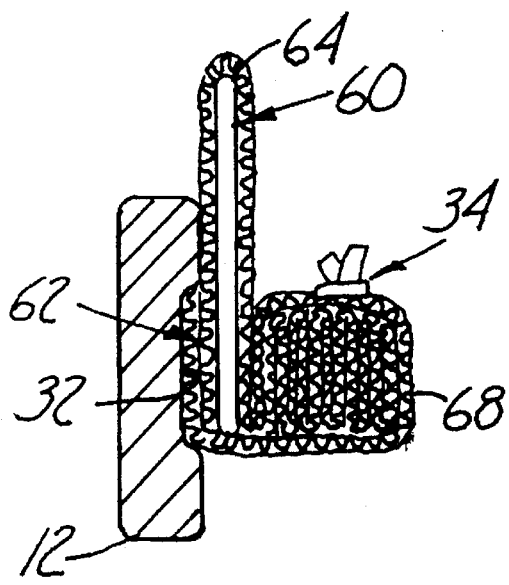
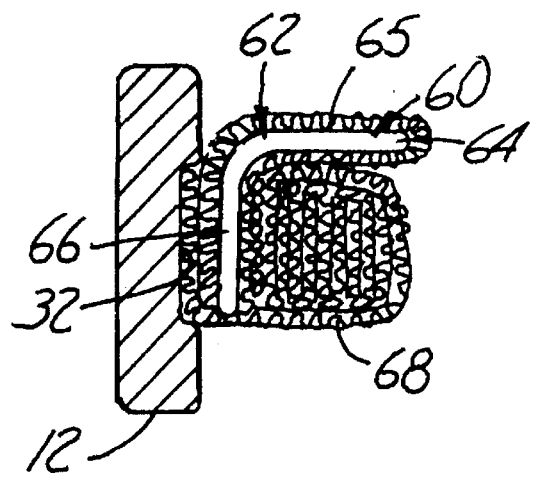
Fig. 6A    Fig. 6B
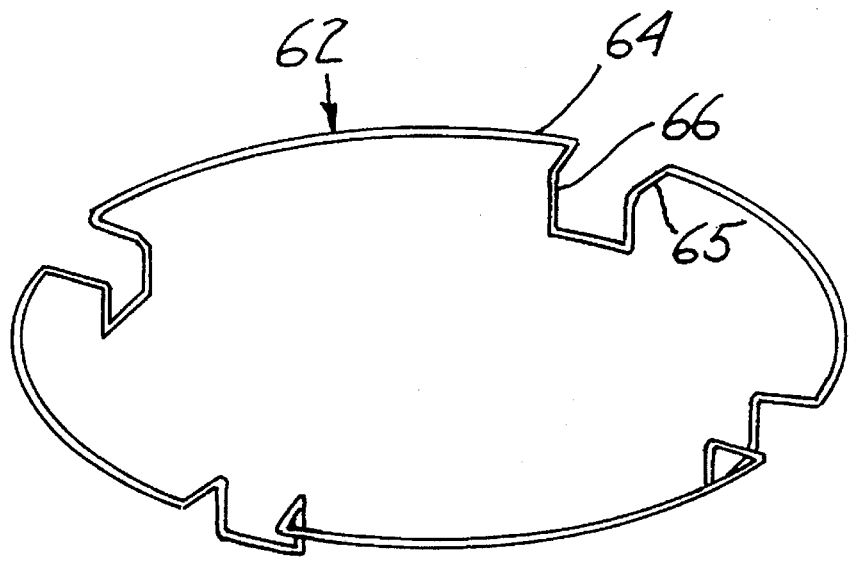
Fig. 6C

SUTURE GUARD FOR PROSTHETIC HEART VALVE

FIELD OF THE INVENTION

The present invention relates to prosthetic heart valves. More specifically, the present invention relates to a shield or guard for covering a suture knot and suture cuff used with a heart valve prosthesis.

BACKGROUND OF THE INVENTION

Heart valve prostheses are used to replace natural heart valves. Prosthetic heart valves include both mechanical heart valves and tissue or bioprosthetic heart valves. In both types, a valving member is carried in an orifice body or housing. In a mechanical heart valve, the valving member typically comprises a mechanical occluder such as a leaflet movable between an open and a closed position. In a tissue valve, the valving member comprises tissue movable between an open and a closed position.

Such prosthetic heart valve prostheses require the orifice to be attached to the tissue annulus left as a result of the surgical excision of the existing valve from the patient's heart. Typically, a sewing or suture cuff is attached to the valve orifice and is used by a surgeon to suture the prosthesis to the heart tissue. Such attachment requires the ends of the suture to be knotted and cut. Following attachment, the suture knots are exposed to blood flow which can cause postoperative complications, prosthesis thrombosis, thromboembolism, excessive tissue ingrowth, or interfere with operation of the valve mechanism.

The concept of covering heart tissue/valve attachment sutures is not new. The concept was described in 1964 in German Patent Application 1180087, entitled "ARTIFICIAL HEART VALVE," by Dr. Wolfgang Seidel. This publication describes a method of attaching heart valves to the native heart tissue annulus. The attachment method uses a ring, which is partially covered with fabric and has protruding "clips." The orifice and occluder are then placed within the clips. The publication mentions the benefit of covering the suture ends and suture knots to reduce thrombus and thrombo-embolic events. The publication primarily focuses on the valve attachment and the use of solid rings.

A more recent patent application, WO 89/00841, by Lillehei, Wang and Brendzel, entitled "PROTECTIVE SHIELD FOR PROSTHETIC HEART VALVES," was published in 1989. The description in this application is of a protective shield which is annular or ring-shaped to fit over a circular valve base and cover an annular sewing ring. The reference mentions methods of installing the ring and various geometries for this ring. The reference describes a separate attachment ring which is attached using sutures, friction, adhesive, a snap fit, hooks, Velcro® or conical friction.

Another patent describing sutures and suture knots is U.S. Pat. No. 3,996,623, issued Dec. 14, 1976, to Robert Kaster, entitled "METHOD OF IMPLANTING A PROSTHETIC DEVICE AND SUTURING MEMBER THEREFOR." This reference discusses a cuff configuration which has two cuff flanges. The native heart tissue annulus is captured in the space provided between the two flanges. The cuff has a flexible cured polymer core which provides resilience to the cuff flanges. The surgeon attaches the distal flange to the distal side of the native tissue with sutures and knots. The suture knots would be located on the proximal side of the tissue annulus. While the cuff/valve is being secured to the native tissue with sutures and knots, the proximal cuff is held "open." After the valve is secured, the proximal flange is released to the closed position. The cuff is secured to the orifice using heat Shrink material. This method of attachment has not been readily accepted by surgeons. The current preferred method of attachment is to use a single flanged cuff which is placed on the proximal side of the native tissue annulus.

SUMMARY OF THE INVENTION

A heart valve prosthesis includes an orifice housing having a lumen formed therethrough. An occluder carried in the orifice housing is movable in the housing between an open position allowing flow through the lumen and a closed position in which flow through the lumen is blocked. A suture cuff is coupled to the orifice housing and extends around an outer circumference of the orifice housing. The suture cuff is used for attaching the heart valve prosthesis to the tissue annulus left in the heart of a patient as a result of the surgical excision of the existing heart valve. A suture extends through the heart tissue annulus and the suture cuff. Opposite ends of the sutures are knotted on top of the suture cuff thereby securing the suture cuff to the heart tissue annulus. A suture shield is coupled to the suture cuff and is movable between an open position in which a suture knot is exposed, and a closed position in which the suture knot and suture cuff are covered.

BRIEF DESCRIPTION OF THE DRAWINGS

FIG. 6A is a cross-sectional view of a suture guard in accordance with another embodiment.

FIG. 6B is a cross-sectional view of a suture guard in accordance with another embodiment.

FIG. 6C is a top perspective view of a spring for use with the suture guard shown in FIGS. 6A and 6B.

DETAILED DESCRIPTION OF THE PREFERRED EMBODIMENTS

A suture guard for use with a heart valve prosthesis is set forth herein which includes an additional flange integral to the proximal side of a sewing or suture cuff. This flange provides a flap of cuff material on the proximal side of the suture cuff which acts as a suture guard and allows a surgeon to cover the suture and suture knots. One suitable heart valve prosthesis is described in U.S. Pat. No. 4,276,658, entitled "HEART VALVE PROSTHESIS," assigned to St. Jude Medical, Inc., of St. Paul, Minn.

Figure 1:
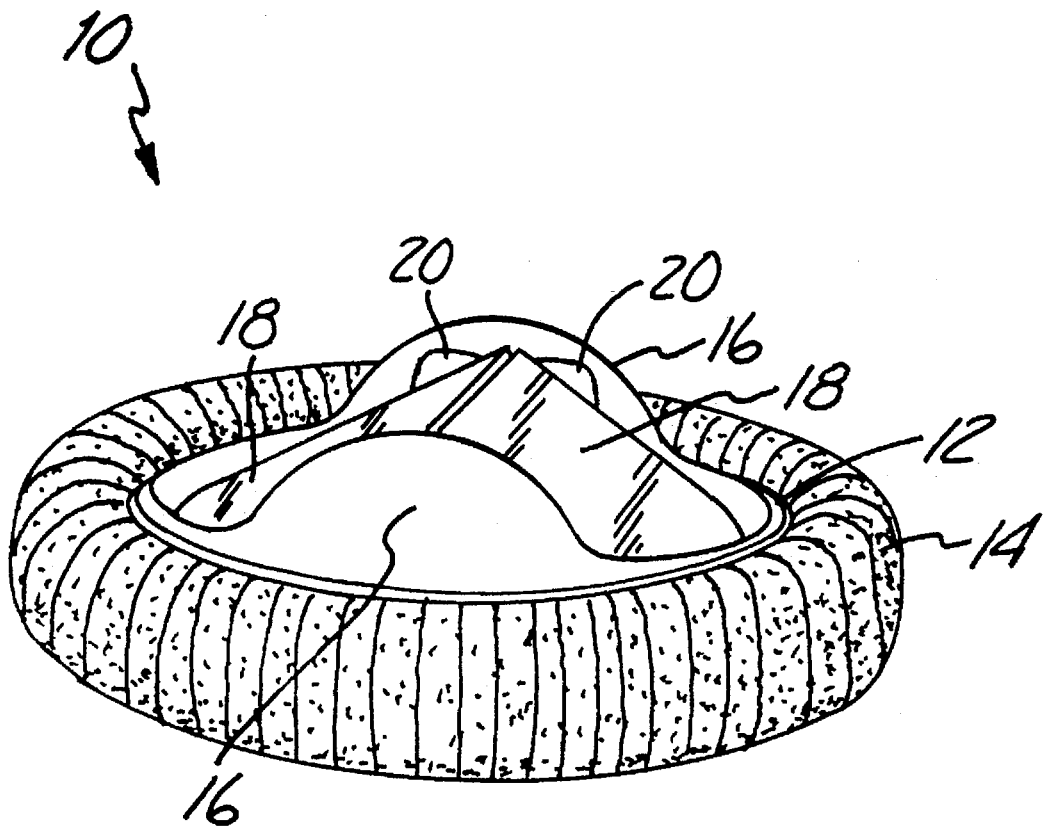
FIG. 1 is a top perspective view of a mechanical heart valve suitable for application of the suture guard techniques set forth herein.

FIG. 1 is a top perspective view of a mechanical heart valve prosthesis 10. Prosthesis 10 is shown generically and the suture guard techniques described hereinafter may be implemented on prosthesis 10, for example. Prosthesis 10 includes orifice housing or body 12. Sewing ring or suture cuff 14 extends around the outer circumference of orifice 12 and is used for attaching valve 10 to the heart tissue annulus that remains when the existing valve of the patient is surgically excised. Orifice 12 includes pivot guards 16 which provide pivots 20 for occluder leaflets 18. A lumen is formed through orifice 12. Occluders 18 move between an open position (not shown), which allows blood flow through the lumen of orifice 12, and a closed position as shown in FIG. 1 which blocks flow therethrough.

Figure 2A:
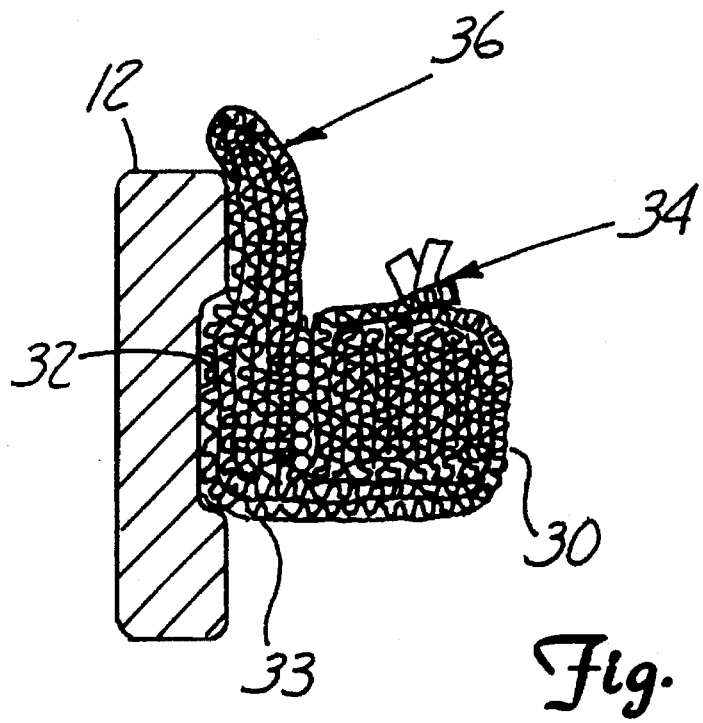
FIG. 2A is a cross-sectional view showing a suture guard in accordance with one embodiment.
Figure 2B:
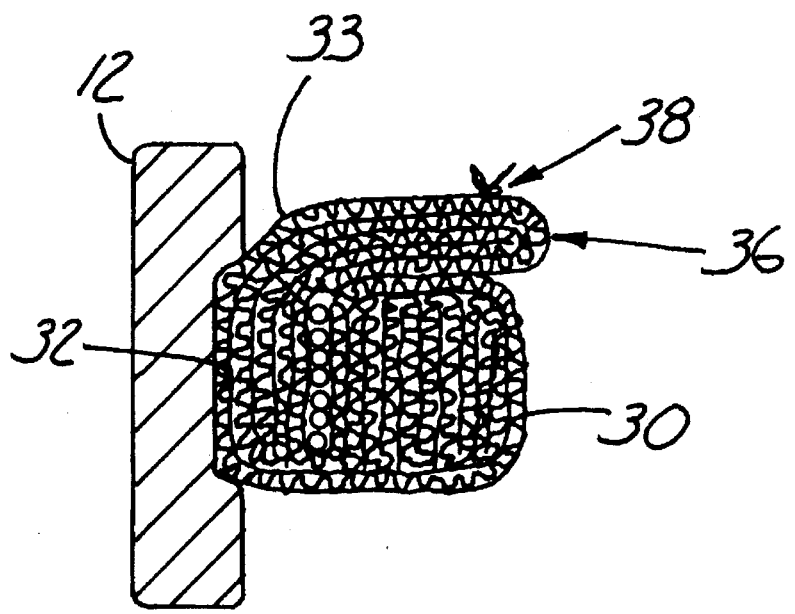
FIG. 2B is a cross-sectional view showing a suture guard in accordance with one embodiment.

FIGS. 2A and 2B are cross-sectional views of a portion of orifice 12 coupled to a suture cuff 30 carried in orifice seat 32 formed in the outer circumference of orifice 12. As used herein, suture cuffs are attached to the valve orifice using any known appropriate technique. For example, the diameter of the cuff may be reduced such that the cuff is secured in a recess which extends around the circumference of the orifice. FIG. 2A shows a suture knot 34 proximate suture cuff 30. A suture guard 36 is shown in FIG. 2A in an open position. Suture guard 36 is shown as a flap extending from an inner radius 33 of cuff 30 which is positioned over suture knot 34. Suture guard 36 is moved to the position shown in FIG. 2A during attachment of cuff 30 to the heart tissue annulus of the patient. In FIG. 2B, suture guard 36 is shown in a closed position in which guard 36 covers suture knot 34 and suture cuff 30. A small secondary suture 38 maintains suture guard 36 in the closed position. Secondary suture 38 is formed of a thinner suture material than the primary suture, and does not require the strength of the primary suture of suture knot 34 used to attach cuff 30 to the tissue annulus. Further, fewer secondary sutures 38 are required to maintain suture guard 36 in a closed position than to secure valve 10 to the tissue annulus.

Figure 3B:
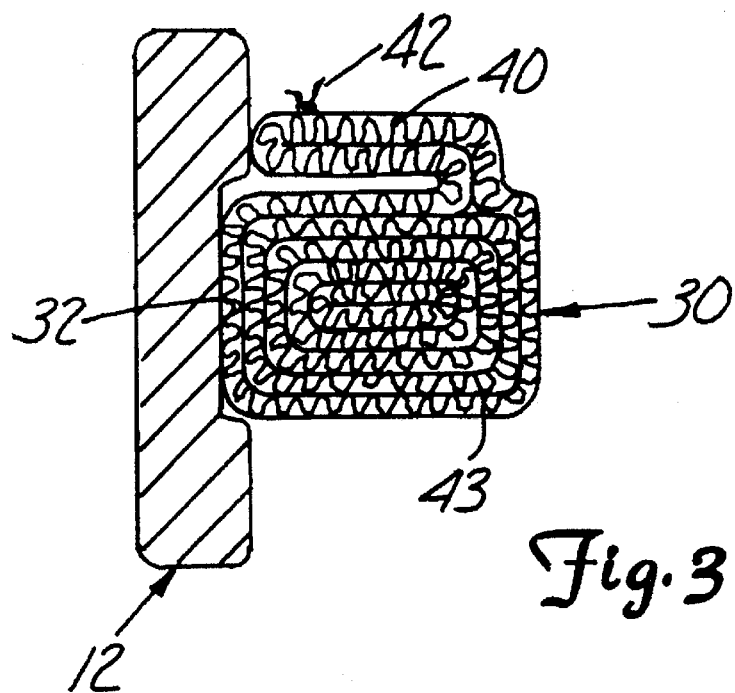
FIG. 3B is a cross-sectional view showing a suture guard in accordance with another embodiment.
Figure 3A:
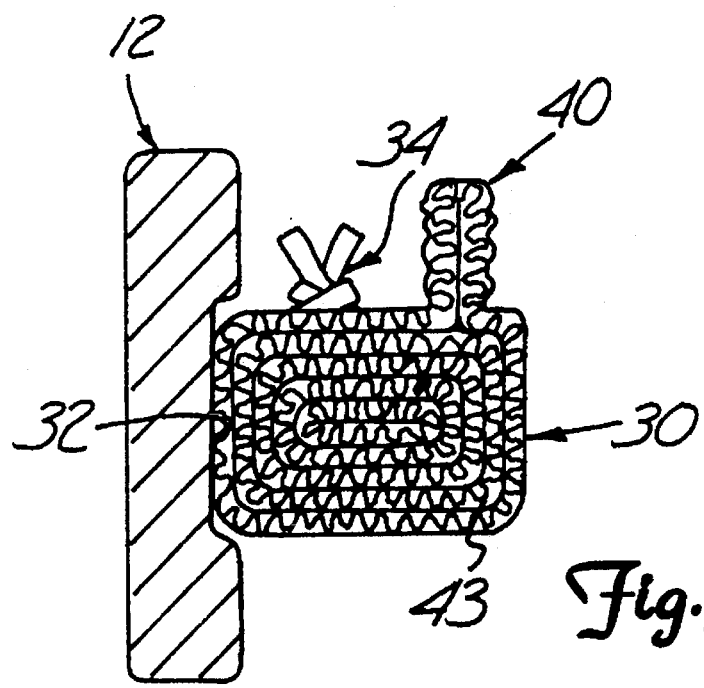
FIG. 3A is a cross-sectional view showing a suture guard in accordance with another embodiment.

FIGS. 3A and 3B show cross-sectional views of another suture guard embodiment. In FIGS. 3A and 3B, a suture guard 40 is positioned on the outer radius 43 of cuff 30 and is shown as being formed integral with cuff 30. This differs from the embodiment of FIGS. 2A and 2B in which suture shield 38 is positioned on an inner radius 33 of cuff 30. FIG. 3A shows suture guard 40 in an open position in which suture knot 34 is exposed. In FIG. 3B, suture guard 40 has been folded over to cover suture cuff 30 and suture knot 34. A smaller secondary suture knot 42 is used to maintain suture guard 40 in the closed position in FIG. 3B, similar to FIG. 2B.

In another embodiment, a biocompatible adhesive is placed between suture guard 40 of FIG. 3A and 3B, or suture guard 36 of FIGS. 2A and 2B, and suture cuff 30. This adhesive replaces secondary suture 38 and secures guard 40 in the closed position. Typically, the suture guard is formed of a compliant material, such as woven polyester or polytetrafluoroethylene (PTFE). A biocompatible glue or fibrin glue may be used to secure the suture guard in the closed position. In this embodiment, the secondary sutures 38 and 42 may not be required.

Another alternative method for fastening the suture guard to the cuff is using hook and loop fasteners, commonly known as Velcro®. In this embodiment, the hook portion of the fastener is located on either the under side of the suture guard or the proximal side of the cuff. The loop is located ion the opposite mating surface as the hook. When the suture guard is maneuvered into place so the knots are covered, the hook and loop fasteners take hold and prevent the guard from revealing the knots.

Figure 4B:
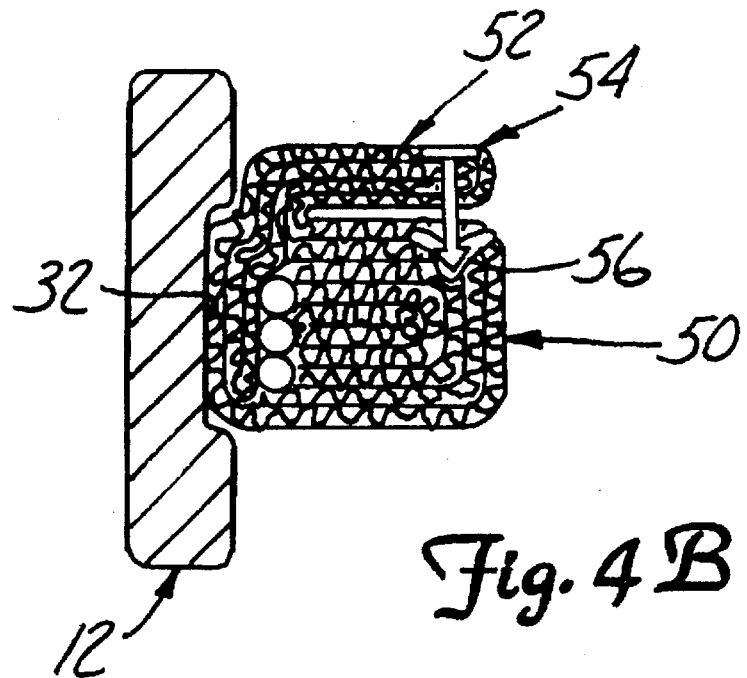
FIG. 4B is a cross-sectional view showing a suture guard in accordance with another embodiment.
Figure 4A:
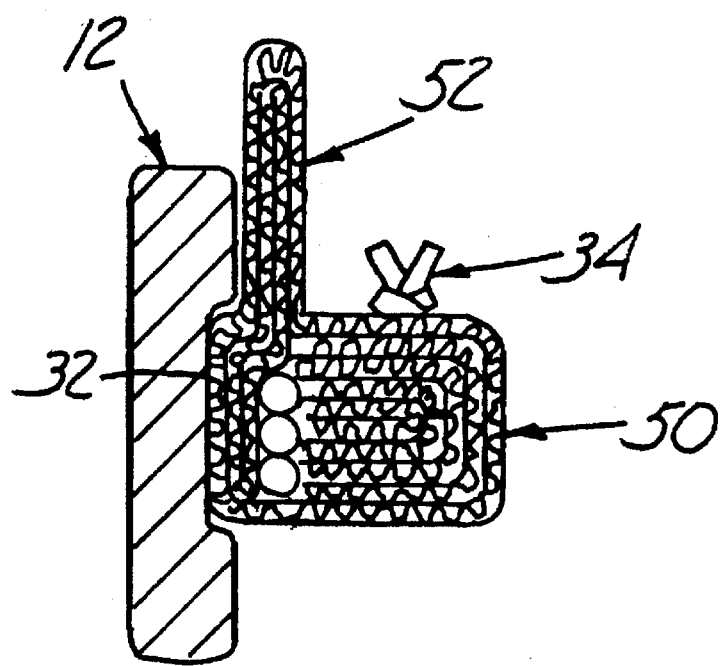
FIG. 4A is a cross-sectional view showing a suture guard in accordance with another embodiment.

FIGS. 4A and 4B show cross-sectional views of a suture guard 52 in accordance with another embodiment. Suture guard 52 is formed integral with and extends from suture cuff 50 and is folded over as shown in FIG. 4B to cover suture cuff 50 and suture knot 34. A barbed fastener 54 is placed through suture guard 52 by a surgeon and into cuff 50 as shown in FIG. 4B. Barbed fastener 54 includes a barbed point 56 which locks fastener 54 in cuff 50. Although suture guard 52 is shown as extending from an interior radius of cuff 50 in FIGS. 4A and 4B, in an alternative embodiment suture guard 52 extends from an exterior radius similar to FIGS. 3A and 3B.

Figure 5B:
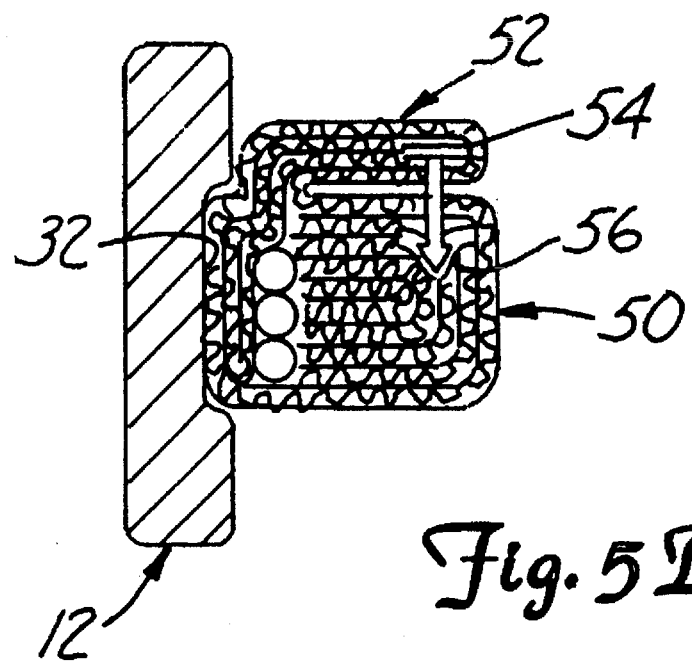
FIG. 5B is a cross-sectional view showing a suture guard in accordance with another embodiment.
Figure 5A:
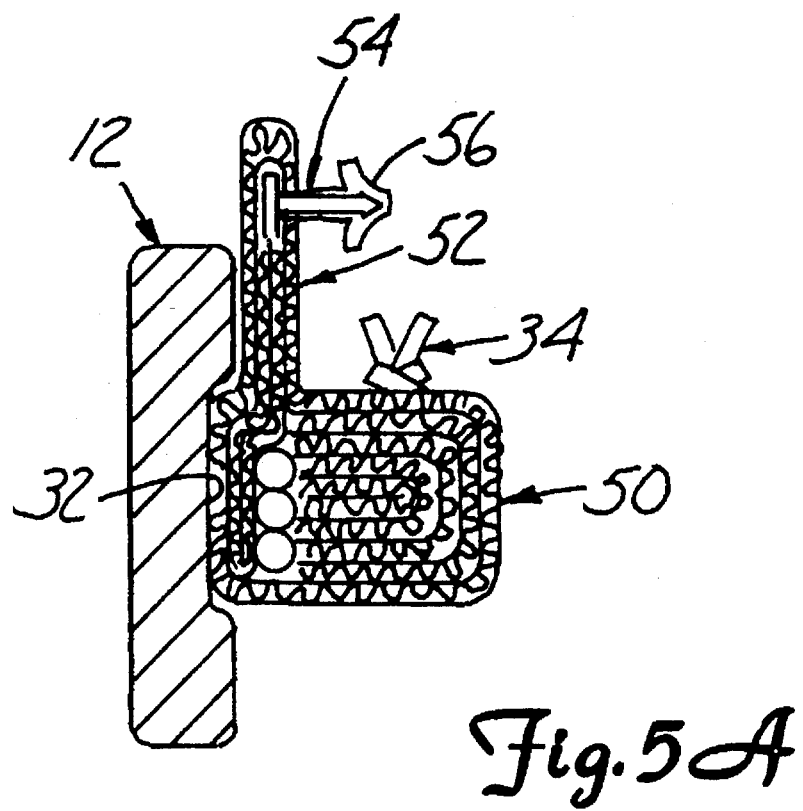
FIG. 5A is a cross-sectional view showing a suture guard in accordance with another embodiment.

FIGS. 5A and 5B are cross-sectional views which show variations on the embodiment of FIGS. 4A and 4B. In FIGS. 5A and 5B, barbed fastener 54 is embedded in the distal end of suture guard 52. The advantage of this technique is that closing of the suture guard 52 as shown in FIG. 5B is faster and easier for the surgeon, and the thrombolic complications associated with additional exposed fastener material are eliminated. Additionally, the barbed fasteners 54 are integral with suture guard 52 for an added measure of safety. Barbed fasteners 54 may be constructed as independent objects or attached to a continuous flexible ring.

One technique for maintaining the suture guard in a closed position is to spring load the suture guard. This may be particularly useful in the case of smaller aortic valves in which it may be difficult to attach the free end of the suture guard to the cuff. A spring or flexible member may be placed on the interior or exterior of the suture guard. In the relaxed position, the spring would maintain the suture guard in a closed position covering the sutures, suture knots and suture cuff without requiring any other securing mechanism. The spring can be moved into a position which exposes the proximal side of the suture cuff (i.e., an open position) allowing the suture cuff to be sutured to the heart tissue annulus by the surgeon FIGS. 6A and 6B show cross-sectional views of a suture guard 60 in accordance with another embodiment which utilizes a spring element 62, as shown in FIG. 6C, to maintain the suture guard 60 in a closed position. FIG. 6C is a top perspective view of wire formed spring element 62 in the closed position shown in FIG. 6B. FIGS. 6A and 6B show suture guard 60 which carries wire formed spring 62 therein as shown in FIG. 6C. Spring 62 includes circumferential portion 64, radial portion 65 and axial portion 66. Radial portion 65 extends into the suture guard 60 and is visible in the cross sections of FIGS. 6A and 6B. The axial portion 66 of spring 62 extends in an axial direction along orifice 12 and is positioned between cuff 68 and orifice seat 32 of orifice 12. Wire formed spring 62 is captured within suture guard 60, and is fixed to orifice 12 along axial portion 66. Preferable materials for wire formed spring 62 include polymers such as acetal, Elgiloy (cobalt-chrome alloy) and MP35N (cobalt-nickel alloy).

Figure 7A:
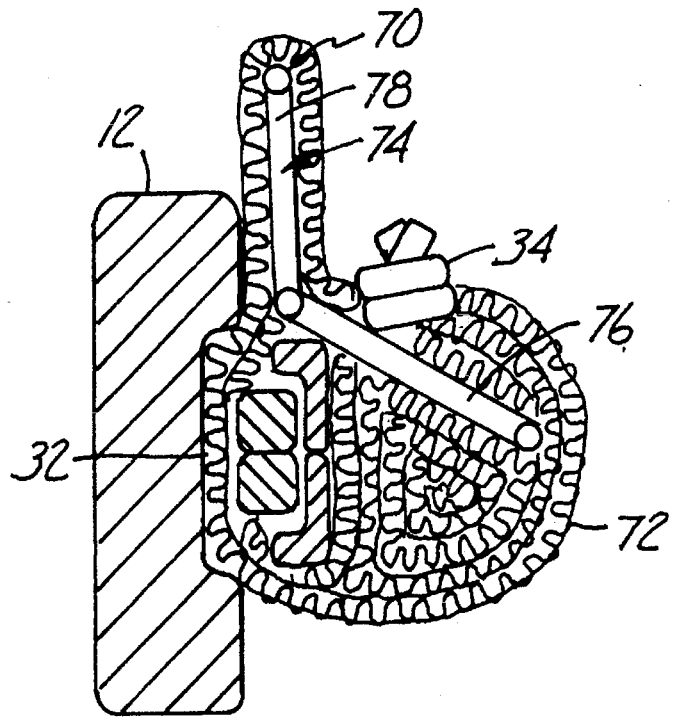
FIG. 7A is a cross-sectional view of a suture guard in accordance with another embodiment.
Figure 7B:
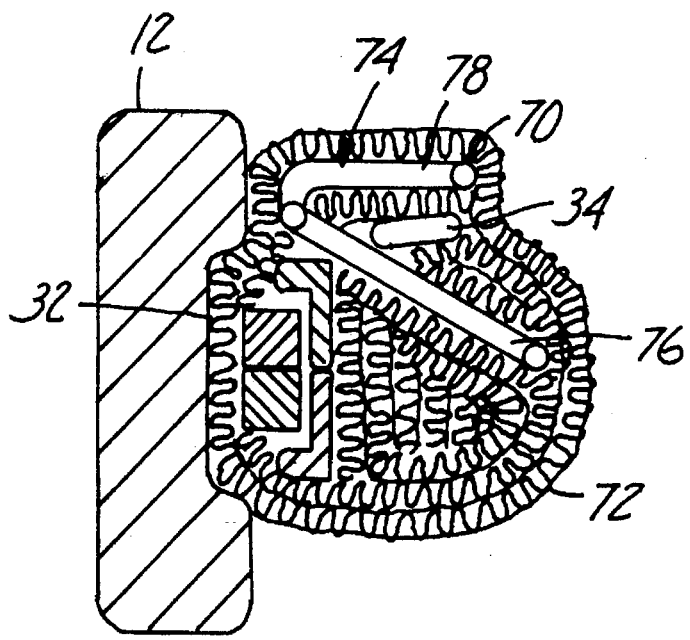
FIG. 7B is a cross-sectional view of a suture guard in accordance with another embodiment.

FIGS. 7A and 7B are cross-sectional views of a spring loaded suture guard 70 in accordance with another embodiment. In FIGS. 7A and 7B, suture guard 70 extends from cuff 72 proximate suture knot 34. An angled spring member 74 is carried in suture guard 70 and cuff 72. A lower portion 76 of spring member 74 is captured in cuff 72 while a movable portion 78 is captured in suture guard 70. Spring 70 is biased to the closed position shown in FIG. 7B. One advantage of this embodiment is that force from spring 70 is applied proximate both sides of suture knot 34 and thus tightly shields knot 34.

Figure 8A:
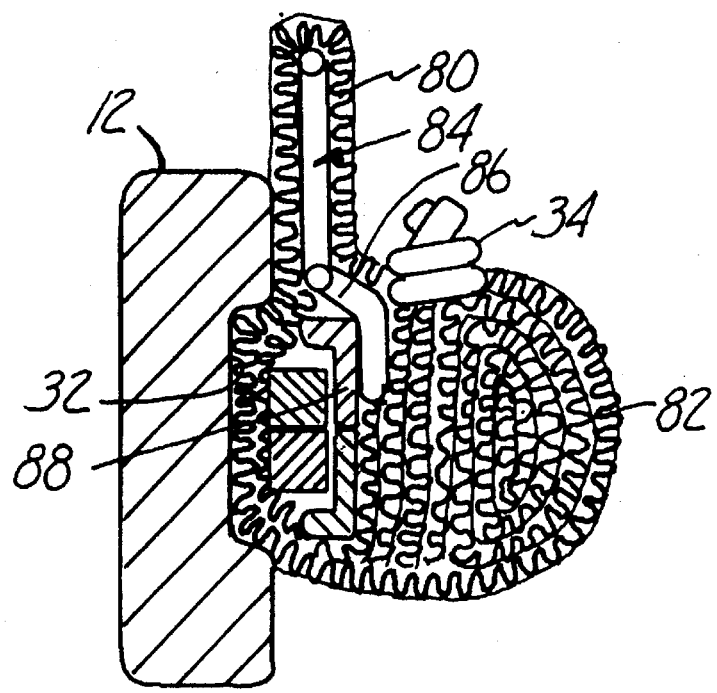
FIG. 8A is a cross-sectional view of a suture guard in accordance with another embodiment.
Figure 8B:
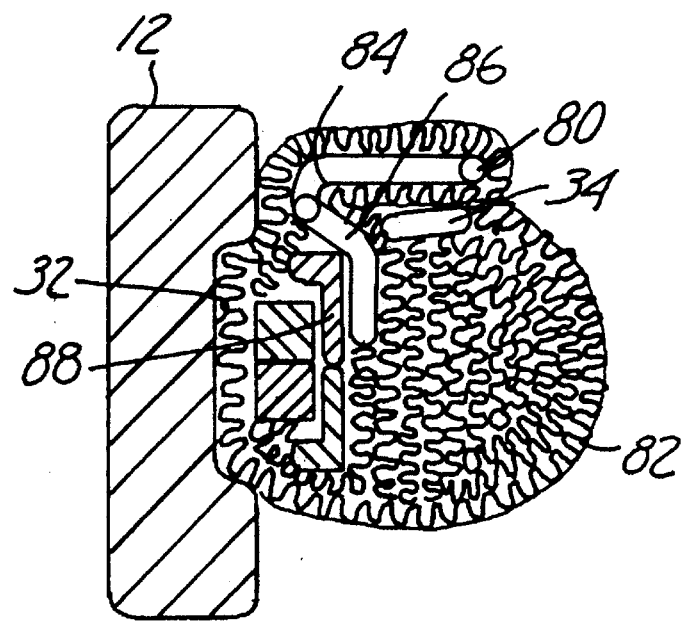
FIG. 8B is a cross-sectional view of a suture guard in accordance with another embodiment.

FIGS. 8A and 8B show cross-sectional views of a spring-loaded suture guard in accordance with another embodiment. Suture guard 80 extends from suture cuff 82 proximate suture knot 34 to cover suture knot 34 and suture cuff 82. A wire formed spring 84 is carried in guard 80 and cuff 82. FIG. 8B shows guard 80 positioned over knot 34 by spring 84. Fixed end 86 of spring 84 is attached to retaining ring 88. Retaining ring 88 secures cuff 82 in orifice seat 32 of orifice 12. Such a ring 88 may be employed in the other embodiments set forth herein. Attachment of fixed portion 86 to retaining ring 88 may be through any appropriate technique such as biocompatible adhesive bonding or welding.

Figure 9A:
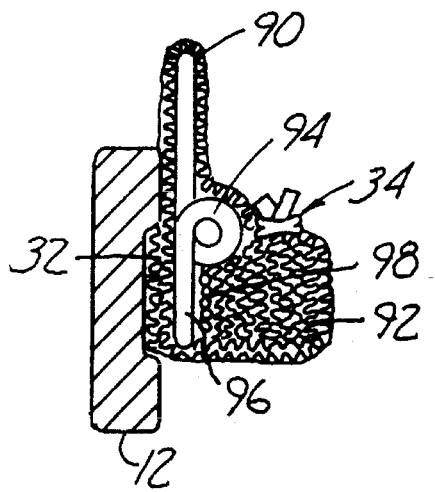
FIG. 9A is a cross-sectional view of a suture guard in accordance with another embodiment.
Figure 9B:
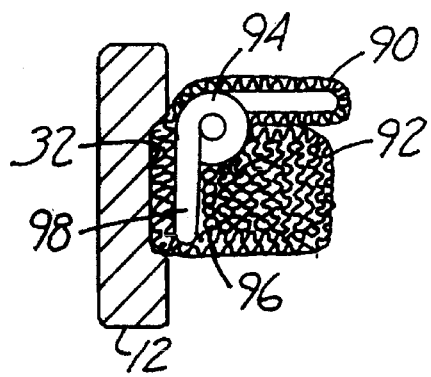
FIG. 9B is a cross-sectional view of a suture guard in accordance with another embodiment.

FIGS. 9A and 9B show cross-sectional views of a spring-loaded suture shield in accordance with another embodiment. Suture guard 90 extends from cuff 92 proximate suture knot 34. A coiled spring 94 is carried in suture guard 90 and cuff 92, and is biased to the closed position shown in FIG. 9B. A fixed end 96 of spring 94 is secured against orifice seat 32 by suture attachment windings 98. A coiled spring is advantageous because deflection of the spring member is less likely to cause permanent deformation from the original biased shape of the spring.

Figure 10:
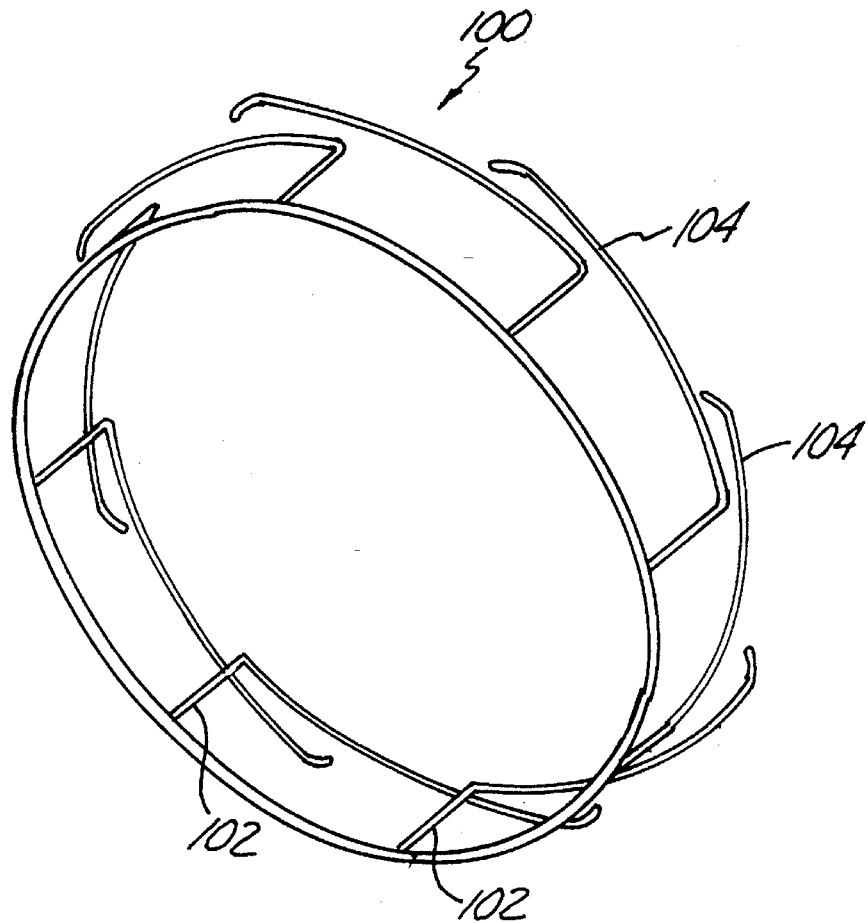
FIG. 10 is a perspective view showing a spring for retaining a suture cuff in accordance with one embodiment.

FIG. 10 is an isometric view of a spring 100 for use with a suture guard in a manner similar to that shown in FIGS. 6A through 9B. Spring 100 includes axial or fixed portions 102 which carry arms 104. Arms 104 are movable between an open position (see FIG. 6A) and a closed position (see FIG. 6B) covering the suture knot. Attachment of spring 100 to orifice 12 would occur at the fixed or axial portion 102 of spring 100.

Figure 11A:
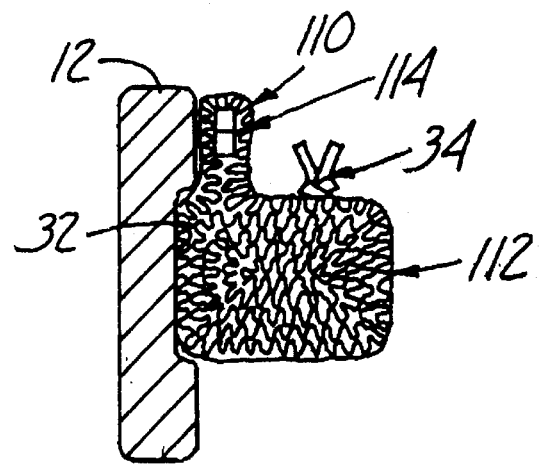
FIG. 11A is a cross-sectional view of a suture guard in accordance with another embodiment.
Figure 11B:
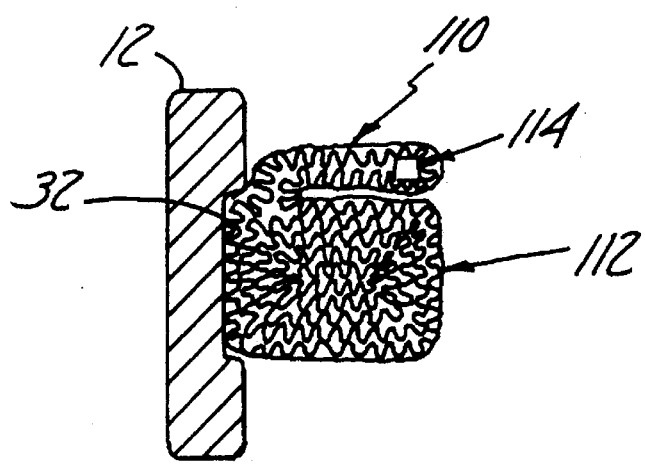
FIG. 11B is a cross-sectional view of a suture guard in accordance with another embodiment.

FIGS. 11A and 11B are cross-sectional views of suture guard 110 in accordance with another embodiment. Suture guard 110 extends from an inner radius of cuff 112 and carries spring member 114 at its distal end. Spring member 114 is an annular spring extending around an outer circumference of suture guard 110. Spring member 114 is biased to a shape which has a diameter greater than or equal to the diameter formed by suture guard 110 in the closed position of FIG. 11B. This causes suture guard 110 to be held in the closed position of FIG. 11B thereby covering suture cuff 112 suture knot 34.

Figure 12A:
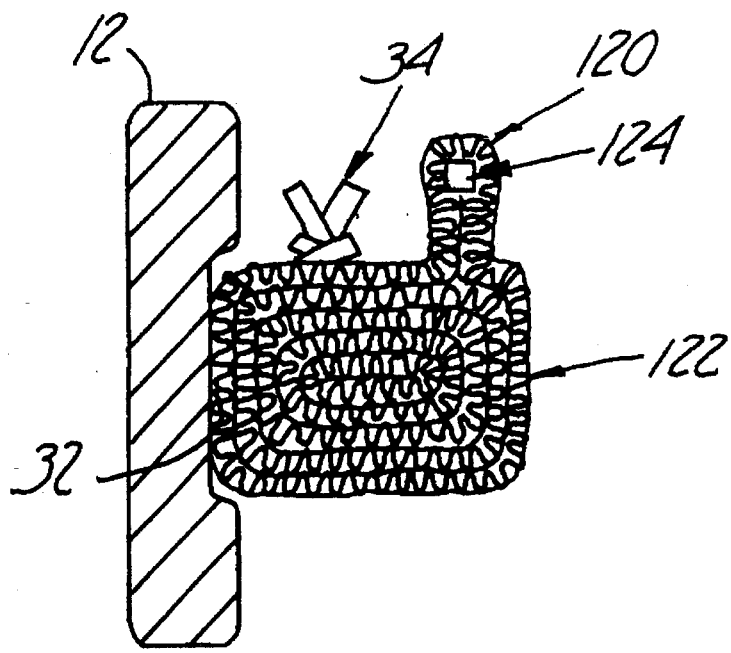
FIG. 12A is a cross-sectional view of a suture guard in accordance with another embodiment.
Figure 12B:
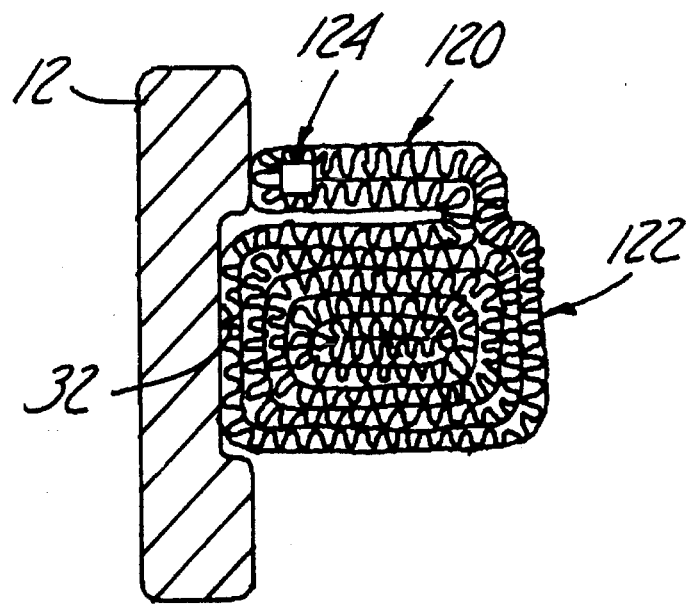
FIG. 12B is a cross-sectional view of a suture guard in accordance with another embodiment.

FIGS. 12A and 12B are cross-sectional views of suture guard 120 in accordance with another embodiment similar to the embodiment of FIGS. 11A and 11B. Suture guard 120 extends from the outer diameter of a suture cuff 122 proximate suture knot 34. The proximal end of suture guard 120 carries annular spring 124. Annular spring 124 is biased to a shape which has a diameter smaller than or equal to the outer diameter of orifice 12. This causes spring 124 to maintain suture guard 120 in the closed position shown in FIG. 12B thereby covering suture knot 34 and suture cuff 122.

Figure 13A:
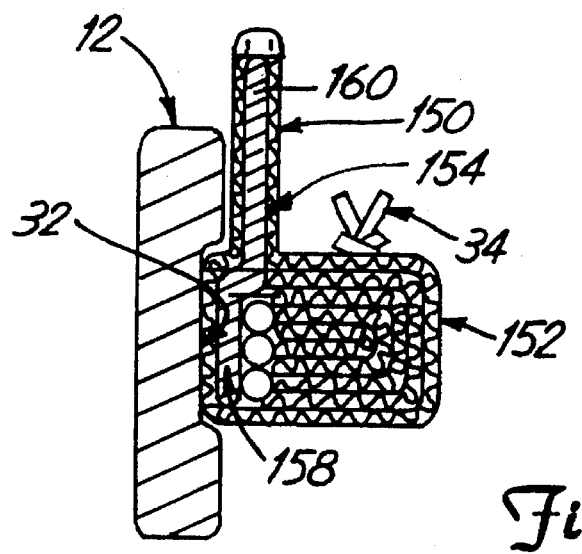
FIG. 13A is a cross-sectional view of a suture guard in accordance with another embodiment.
Figure 13B:
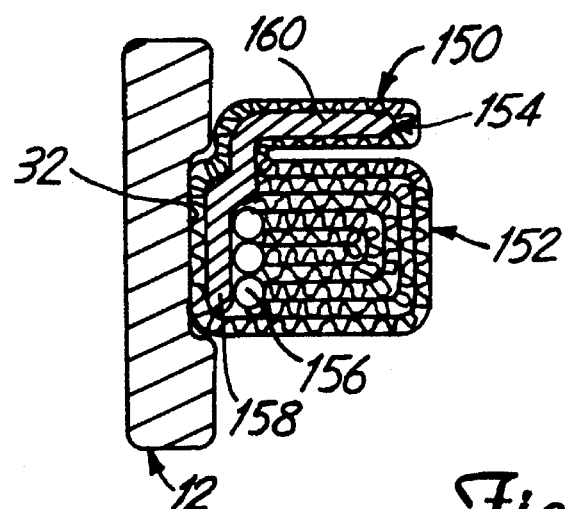
FIG. 13B is a cross-sectional view of a suture guard in accordance with another embodiment.
Figure 13C:
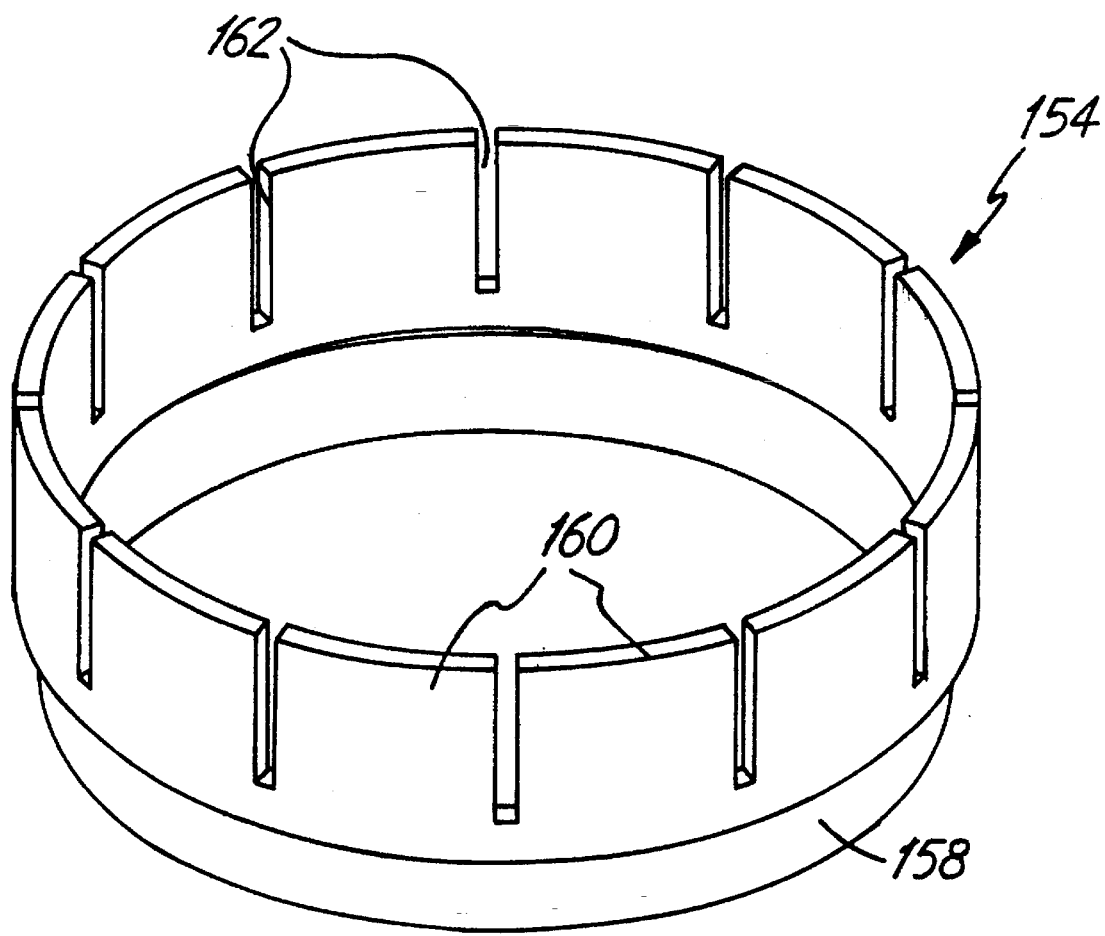
FIG. 13C is a top perspective view of a member for maintaining a suture guard in a closed position in accordance with the invention.

FIGS. 13A and 13B show cross-sectional views of suture guard 150 in accordance with another embodiment. Suture guard 150 extends from suture cuff 152 attached to orifice 12 at orifice seat 32. Spring insert 154 is carried in suture guard 150 and cuff 152. Insert 154 is secured against orifice seat 32 with suture windings 156. FIG. 13C is a top perspective view of insert 154. Insert 154 includes fixed portion 158 and movable portions 160 which is used to cover suture cuff 152 and suture knot 34. Movable portions 160 are separated by gaps 162 which allow movable portions 160 to be deflected radially outward. Insert 154 is biased to the closed position shown in FIG. 13B such that suture guard 150 covers suture knot 34.

Figure 14A:
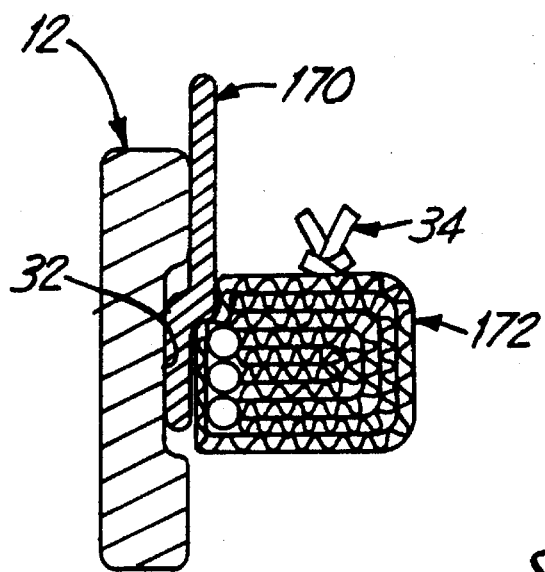
FIG. 14A is a cross-sectional view of a suture guard in accordance with another embodiment.
Figure 14B:
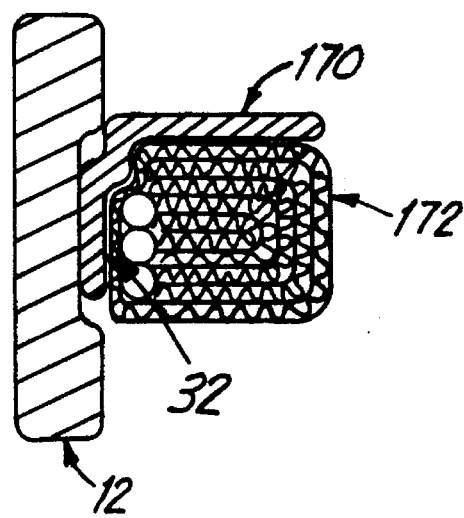
FIG. 14B is a cross-sectional view of a suture guard in accordance with another embodiment.

FIGS. 14A and 14B show another embodiment in which a spring element suture guard 170 directly covers knot 34 and suture cuff 172. Suture guard 170 may be formed similar to insert 154 shown in FIG. 13C. This embodiment may be advantageous if tissue growth is not desired or to control tissue growth. For example, guard 170 can be formed of a material which does not promote tissue ingrowth such as metals or polymers. Alternatively, guard 170 may be formed of a material which promotes controlled tissue ingrowth such as a polymer impregnated with a biologically responsive chemical. In another embodiment which is not shown, adjacent portions 160 shown in FIG. 13C overlap each other such that in the radially outward position the entire suture cuff is completely covered.

Attachment of the fixed portion of the springs set forth herein may be through any appropriate technique. For example, suture windings, retainer rings, stiffening rings or stents may be employed. The members are manufactured from biocompatible materials such as metals or polymers, for example.

In the embodiments of FIGS. 6A through 10 and 13A through 14B, the spring member can be replaced with a malleable material. The initial shape of the material is in the open position. After a surgeon has fixed the valve to the heart tissue, the surgeon pushes or forms the malleable material over the suture and suture knots. This may be accomplished by either using the surgeon's finger or a tool. Further, a malleable material may be employed in the embodiments of FIGS. 6A through 9B. Suitable examples of malleable materials include polymers or metals such as tantalum or titanium.

The embodiments set forth in FIGS. 3 through 14 may be manufactured from materials which are temperature responsive. In these materials, a change in temperature causes the suture guard to move to the closed position. There are numerous materials which have this quality. For example, Nitinol®, manufactured by Minnesota Mining & Manufacturing Company of St. Paul, Minn., and heat polymer materials such as heatshrink polyester may be employed. Nitinol® is a nickel titanium alloy which can be deformed and which will remain in the deformed shape until heat is applied. In the present invention, the material would be deformed such that the suture guard is in the open position. After suturing is complete, the surgeon applies heat to activate the material causing the guard to assume its closed position. Application of heat by warmed cardioplegia solution causes the material to deform to its original heat-set condition. This provides a quick and easy technique for the surgeon to cover the suture and suture knots. A polyester heat shrink material which contracts radially inward to a closed position may also be employed. For example, this could be used in the embodiment shown in FIGS. 12A and 12B.

Figure 15A:
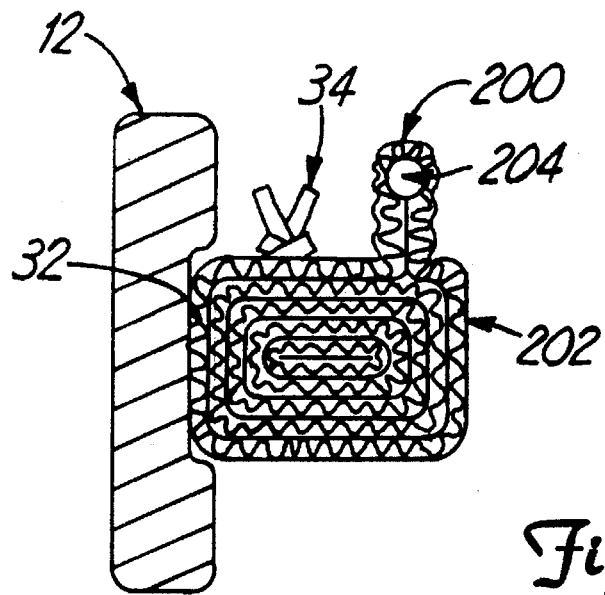
FIG. 15A is a cross-sectional view of a suture guard using a drawstring technique.
Figure 15B:
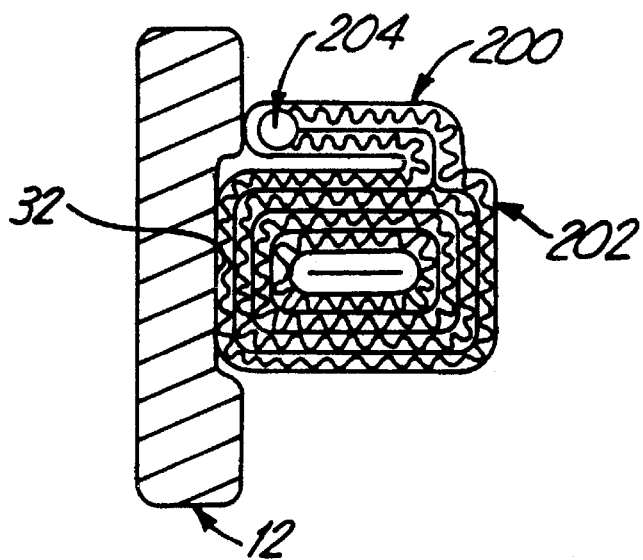
FIG. 15B is a cross-sectional view of a suture guard using a drawstring technique.
Figure 15C:
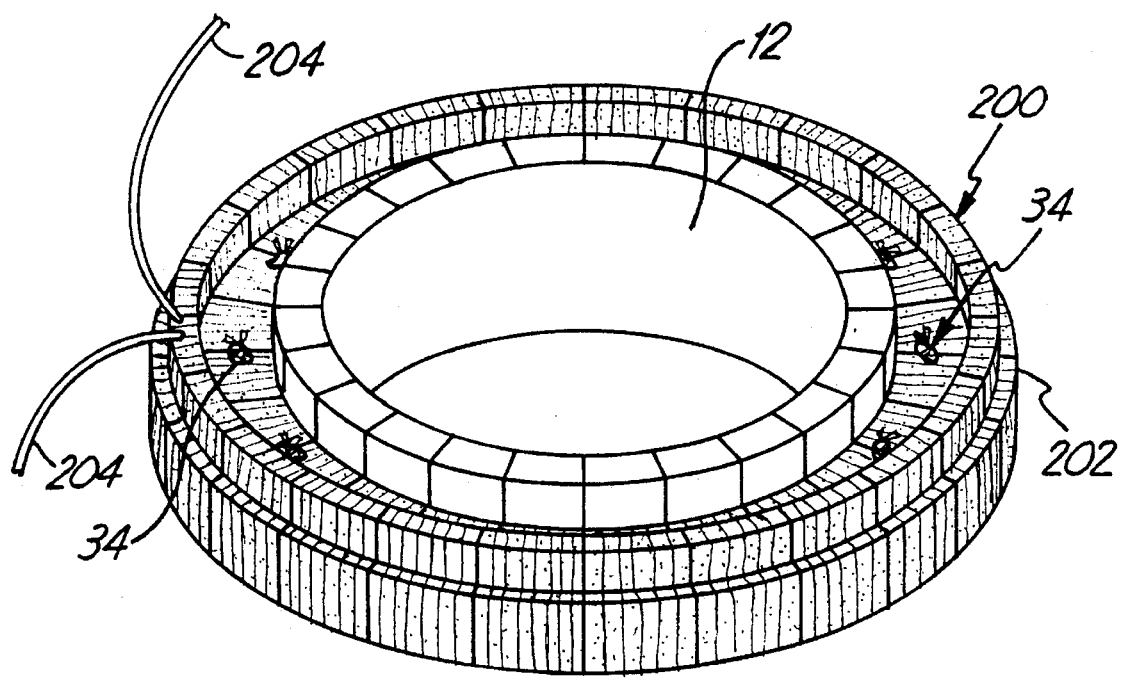
FIG. 15C is a top plan view of the suture guard of FIGS. 15A and 15B in an open position.
Figure 15D:
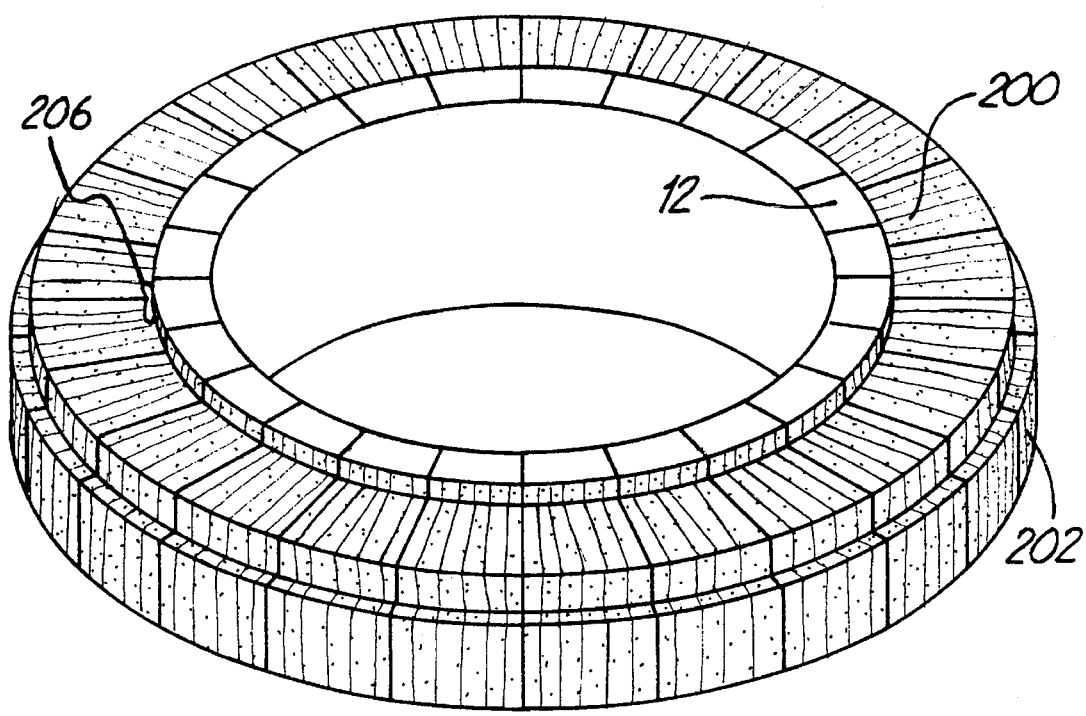
FIG. 15D is a top plan view of a suture guard of FIGS. 15A and 15B in a closed position.

Another technique for restraining the suture guard is through the use of drawstring sutures. Using this techniques, sutures are placed within the proximal end, with respect to the surgeon, of the suture guard. FIGS. 15A through 15D show such a drawstring technique. FIGS. 15A and 15B are cross-sectional views showing suture guard 200 extending from the outer radius of suture cuff 202. A drawstring 204 extends through the proximal end of suture guard 200. As shown in FIG. 15B, in the closed position suture guard 200 covers knot 34. FIG. 15C is a top perspective view of suture guard 200 in the open position, as depicted in FIG. 15A. In this position, cuff 202 is exposed allowing the surgeon to form suture knots 34. After suturing is complete, the surgeon pulls drawstring 204 to move suture guard 200 to the position shown in FIG. 15D. In FIG. 15D, drawstring 204 has been tightened causing guard 200 to be pulled inward, thereby covering suture knots 34. Knot 206 is formed from drawstring 204 and may be placed under suture guard 200 thereby covering knot 206. Note that in FIGS. 15C and 15D, pivot guards and occluder leaflets have not been shown for simplicity.

Figure 16A:
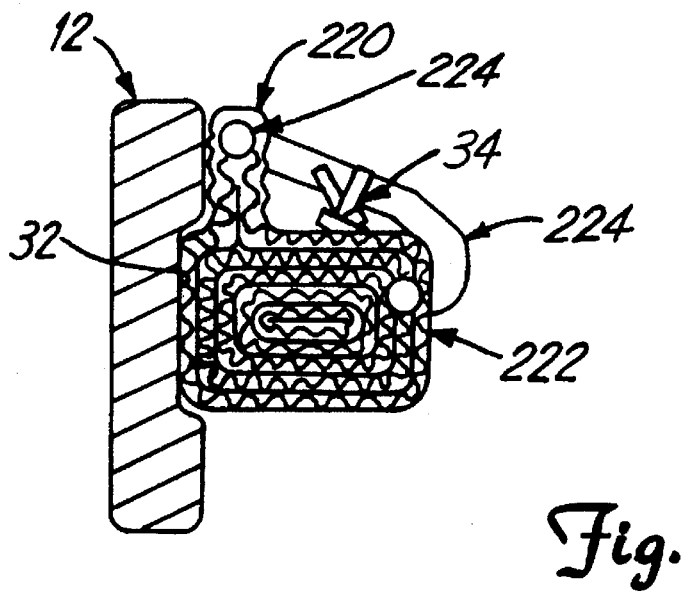
FIG. 16A is a are cross-sectional view of a suture guard using a drawstring technique.
Figure 16B:
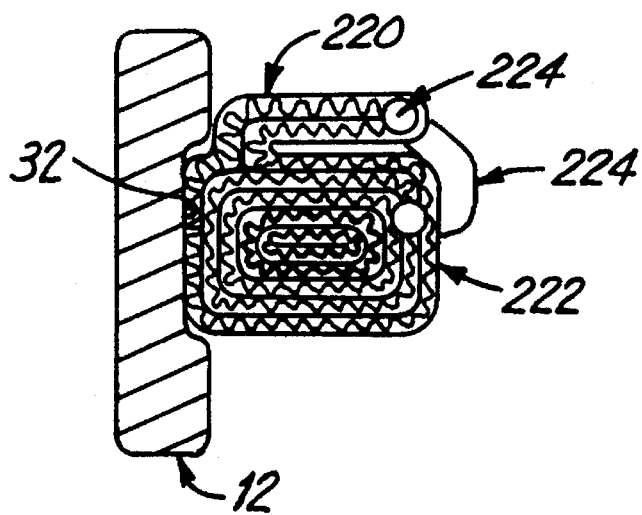
FIG. 16B is a are cross-sectional view of a suture guard using a drawstring technique.
Figure 16C:
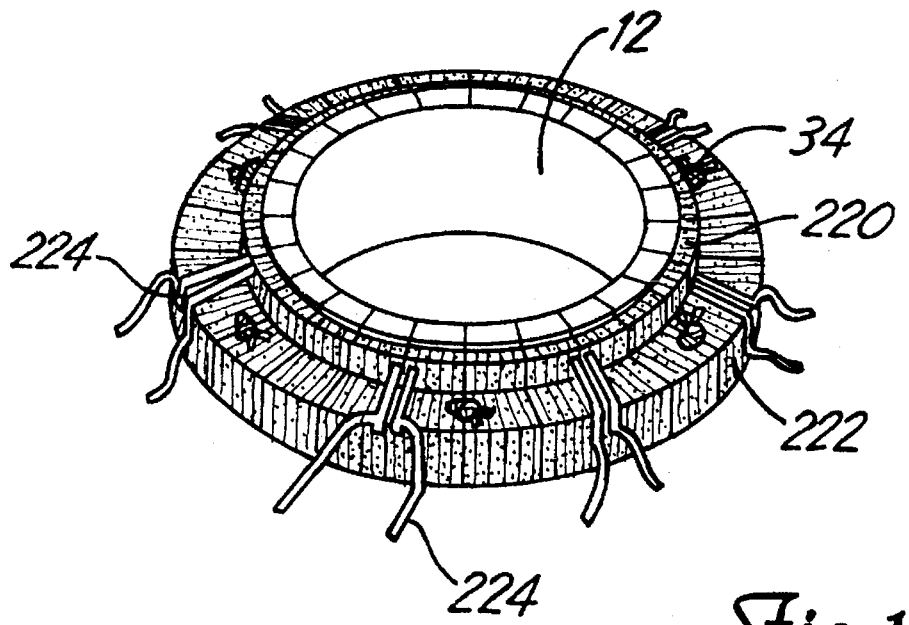
FIG. 16C is a top plan view of the suture guard of FIGS. 16A and 16B in an open position.
Figure 16D:
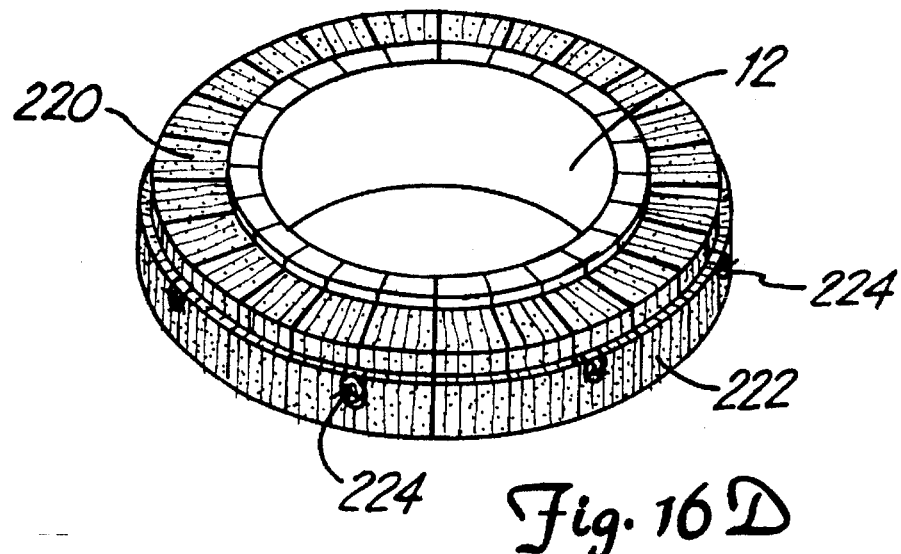
FIG. 16D is a top plan view of a suture guard of FIGS. 16A and 16B in a closed position.

FIGS. 16A through 16D show another technique using drawstrings to implement a suture guard. FIGS. 16A and 16B are cross-sectional views showing suture guard 220 extending from the inner radius of suture cuff 222. Drawstring 224 is carried through the proximal end of suture guard 220 and extends into the outer radius of suture cuff 222. As shown in FIG. 16B, drawstring 224 is tightened thereby closing suture guard 220. FIG. 16C is a top perspective view showing orifice 12 having suture guard 220 in an open position. As shown in FIG. 16C, drawstrings 224 loop through suture guard 220 and suture cuff 222. As the surgeon pulls drawstrings 224, suture guard 220 is moved to the closed position as shown in the perspective view of FIG. 16D. After cinching drawstrings 224, the drawstrings are knotted thereby securing suture guard 220 in the closed position as shown in FIG. 16D. The drawstring embodiments are advantageous because the suturing techniques are familiar and expected by surgeons.

In another embodiment, magnets may be employed in the suture cuff and suture guard to maintain the suture guard in a closed position. The suture guard set forth herein is formed of biocompatible materials.

The suture guard set forth herein provides a two-flange system which allows a surgeon to attach the valve using a preferred method of placing the attachment portion of the cuff on the proximal side of the native heart tissue annulus. The suture guard can be used with any suturing technique such as everted mattress sutures, non-everting mattress sutures, figure of eight sutures or continuous sutures. The suture guard is formed integral with the cuff/valve assembly. The suture guard is easily manufactured and can be easily used by surgeons with their preferred attachment methods. The suture guard can be adapted and implemented with most existing heart valve prostheses. Some of the embodiments are self-actuated and will engage the suture knot upon release by the surgeon. The suture guard tends to be flexible because it lies on the attachment portion of the cuff and therefore has the ability to conform to the irregularities commonly encountered in native heart tissue.

Although the present invention has been described with reference to preferred embodiments, workers skilled in the art will recognize that changes may be made in form and detail without departing from the spirit and scope of the invention. For example, although the specification has discussed mechanical heart valves, the techniques set forth herein are also applicable to tissue valves (bioprostheses). In addition, typical materials are described in many of the preferred embodiments. However, applicable materials shall not be limited to those mentioned. Applicable material include any biocompatible polymer, metal or other material that provides the mechanical characteristics described for the embodiments.

What is claimed is:

1. A heart valve prosthesis, comprising;

an orifice housing having an exterior circumference and providing a lumen therethrough;

an occluder movable in the orifice housing between an open position allowing flow through the lumen and a closed position in which flow through the lumen is blocked;

a suture cuff extending around the exterior circumference and coupled to the orifice housing, the suture cuff adapted for receiving a suture therethrough for attaching the prosthesis to a heart tissue annulus, wherein the suture cuff provides a suture knot surface for carrying a suture knot thereon; and a suture guard movably attached to the suture cuff and movable between an attached open position in which the suture knot surface is exposed and a closed position covering the suture knot surface and a suture knot carried on the suture knot surface.

2. The heart valve prosthesis of claim 1 including an adhesive securing the suture guard in the closed position.

3. The heart valve prosthesis of claim 1 including a barb coupled to the suture guard which secures the suture guard to the suture cuff in the closed position.

4. The heart valve prosthesis of claim 1 including a bendable element carried in the suture guard.

5. The heart valve prosthesis of claim 1 wherein the suture guard attaches to the suture cuff proximate an inner radius of the suture cuff and extends in a generally radially outward direction when in the closed position.

6. The heart valve prosthesis of claim 1 wherein the suture guard attaches to the suture cuff proximate an outer radius of the suture cuff and extends in a generally radially inward direction when in the closed position.

7. The heart valve prosthesis of claim 1 further comprising a spring member coupled to the suture guard which maintains the suture guard in the closed position.

8. The heart valve prosthesis of claim 7 wherein the spring member is coupled to the orifice housing.

9. The heart valve prosthesis of claim 7 wherein the spring member includes a coil.

10. The heart valve prosthesis of claim 7 wherein the spring member comprises an annular spring.

11. The heart valve prosthesis of claim 1 wherein the suture guard is maintained in the closed position by a member coupled to the suture guard.

12. The heart valve prosthesis of claim 11 wherein the member is carried within the suture guard.

13. The heart valve prosthesis of claim 11 wherein the member is positioned on a side of the suture guard opposite the suture cuff when the suture guard is in the closed position.

14. The heart valve prosthesis of claim 1 further comprising a magnet coupled to the suture guard and the suture cuff is positioned to maintain the suture guard in the closed position.

15. The heart valve prosthesis of claim 1 further comprising a drawstring carried in the suture guard to maintain the suture guard in the closed position when the drawstring is cinched.

16. The heart valve prosthesis of claim 15 wherein the drawstring extends through suture cuff.

17. The heart valve prosthesis of claim 15 further comprising a plurality of drawstrings.

18. The heart valve prosthesis of claim 1 wherein the suture guard is integral with the prosthesis.

* * * * *